(12) United States Patent
Hsiung et al.

(10) Patent No.: US 7,719,427 B2
(45) Date of Patent: May 18, 2010

(54) WIRELESS PH MEASUREMENT SYSTEM

(75) Inventors: Shen-Kan Hsiung, Tao-Yuan (TW); Jung-Chuan Chou, Tao-Yuan (TW); Tai-Ping Sun, Tao-Yuan (TW); Jun-Jie Feng, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 943 days.

(21) Appl. No.: 11/465,780

(22) Filed: Aug. 18, 2006

(65) Prior Publication Data

US 2008/0041721 A1    Feb. 21, 2008

(51) Int. Cl.
*G08B 23/00* (2006.01)

(52) U.S. Cl. ............. 340/573.1; 340/572.1; 204/415; 204/433; 600/424

(58) Field of Classification Search ......... 340/573.1, 340/572.1; 200/433, 415; 600/300
See application file for complete search history.

(56) References Cited

U.S. PATENT DOCUMENTS

| | | | | |
|---|---|---|---|---|
| 3,547,794 A | * | 12/1970 | Iida et al. ............ | 204/420 |
| 3,888,237 A | * | 6/1975 | Mori .................. | 600/350 |
| 4,381,011 A | * | 4/1983 | Somers, III .......... | 600/350 |
| 7,366,468 B2 | * | 4/2008 | Yoshida .............. | 455/456.1 |
| 7,539,551 B2 | * | 5/2009 | Komura et al. ....... | 700/94 |
| 7,647,090 B1 | * | 1/2010 | Frisch et al. ........ | 600/473 |
| 2006/0023738 A1 | * | 2/2006 | Sanda ................ | 370/463 |
| 2006/0270940 A1 | * | 11/2006 | Tsukashima et al. .. | 600/529 |
| 2007/0068811 A1 | * | 3/2007 | Tsukashima et al. .. | 204/433 |

* cited by examiner

*Primary Examiner*—Eric M Blount
(74) *Attorney, Agent, or Firm*—WPAT, PC; Justin King

(57) ABSTRACT

A wireless pH measurement system is disclosed, the wireless pH measurement system includes a portable module and a receiver end. The portable module comprises a signal detecting and processing portion and a wireless transmission portion. The signal detecting and processing portion comprises a sensor unit for detecting a pH signal, amplifying, filtering noise, analog/digital conversion and numerical processing to generate a pH measurement signal. The wireless transmission portion receives the pH measurement signal via a transmission interface and transmits by a Bluetooth module. The receiver end includes a Bluetooth receiver for receiving the pH measurement signal. The receiver end processes the pH measurement signal by programs, displays, analyzes and stores the pH measurement signal and transmits warning signal when an abnormal pH measurement signal is received.

27 Claims, 6 Drawing Sheets

| Transmission technique | Bluetooth | IrDA | Home RF | Wireless Local Area Network (IEEE 802.11) |
|---|---|---|---|---|
| Wireless medium(GHz) | 2.4 | Infrared | 2.4 | 2.4 or 5 |
| Data transmission rate (Mbps) | 1 | 1-16 | 1 | 1-54 |
| Range (m) | 10 or 100 | <10 | 50 | >50 |
| Cost (%USD) | $9 | 少 | >$50 | >$100 |

Table 1

| pH value / Samples | 1.95 | 3.85 | 5.95 | 7.39 | 9.47 | 11.73 |
|---|---|---|---|---|---|---|
| No.1 | 2.39 | 4.32 | 6.42 | 8.1 | 9.4 | 11.9 |
| No.2 | 2.12 | 4.4 | 6 | 8 | 9.8 | 12.3 |
| No.3 | 2.12 | 4.3 | 5.4 | 7.7 | 9.8 | 11.8 |
| No.4 | 2.14 | 3.8 | 5.9 | 7.8 | 9.9 | 11.8 |
| No.5 | 2.2 | 4.1 | 6 | 7.9 | 9.9 | 11.9 |
| No.6 | 2.3 | 3.9 | 6.1 | 7.9 | 9.8 | 11.8 |
| No.7 | 2.1 | 4.2 | 5.9 | 8.1 | 9.9 | 12.4 |
| No.8 | 2.1 | 4.17 | 6.14 | 7.34 | 9.6 | 11.3 |
| No.9 | 2.1 | 4.1 | 6.14 | 8 | 10.2 | 12.11 |
| No.10 | 2.3 | 4.2 | 6 | 7.9 | 9.3 | 11.7 |

Table 2

WIRELESS PH MEASUREMENT SYSTEM

BACKGROUND OF THE INVENTION

1. Field of the Invention

The present invention is generally related to a wireless pH measurement system, and more particularly to a wireless pH measurement system fabricated by semiconductor processes.

2. Description of the Prior Art

With the advance in economics, the standard of living becomes higher and the life style and diet are also drastically changing. Thus, modern people become over-nourishment to have many chronic diseases, such as hypertension, diabetes, gout, heart disease. Therefore, household medical equipments will be important equipments for every family. Before measuring the pH value in blood, it should be understood that the pH value in blood is important to human body and how diet affects human body.

The acidity or basicity of food does not depend on taste but is the result from digesting food and metabolizing by human body. After metabolism, if the food generates more ions, like phosphate ion, sulfate ion, chloric ion, it forms acids in human body to generate acidic reaction. If the food generate more ions, like sodium ion, potassium ion, magnesium ion, calcium ion, it forms base in human body to generate basic reaction. It is also related to the mineral content in the food. Generally, those including more sulfur and/or phosphor mineral matters belong to acidic food while those including more potassium, magnesium, calcium mineral matters belong to basic food.

Food intake is preferably controlled to be acid-base balance. Although the acidity or basicity of food only has very tiny influence to human body, nutrition is unbalanced if intake is too acidic or basic and health will be affected after a long period of time. Human body has a good acid-base buffer system to maintain body fluid at a constant pH value, about in the range of pH7.35~pH7.4. However, it is still important to have balanced food intake.

The so-called acidic food means that the food generates more anions, such as phosphate ion ($PO_4^{3-}$), sulfate ion ($SO_4^{2-}$), chloric ion ($Cl^-$), than cations, such as sodium ion ($Na^+$), potassium ion ($K^+$), magnesium ion ($Mg^{2+}$), calcium ion ($Ca^{2+}$) and thus these excess amount of anions form acid to generate acid reaction. On the contrary, it is basic food if generating more cations than anions. Therefore, those including more sulfur and/or phosphor mineral matters belong to acidic food while those including more potassium, magnesium, calcium mineral matters belong to basic food.

A pH sensor can use an ion sensitive field effect transistor as its electrode, the sensing principle of which is described as follows. The ion sensitive electrode is placed in an unknown solution. The total amount of ions diffusing to the interface electric double layer changes along with the concentration of the ions in the unknown solution. The ions diffusing to the electric double layer are electrically attracted by ion selective substances so as to combine to each other. While the tested ions approach the voltage type sensing electrode, the electrode has voltage induction so as to generate an electric potential signal because ion itself has either positive charge or negative charge.

Ion sensitive field effect transistors have the advantages of miniaturizability and mass production, low cost, high input impedance and low output impedance, fast response, compatibility with MOSFET processes. In addition, many related papers have been reported [Jia Yong-Long, "Study of the extended gate field effect transistor (EGFET) and signal processing IC using the CMOS technology", June, 2001, Department of electrical engineering, Chung Yuan Christian University, Ph. D. dissertation, pp. 1-12 and 85-97; Chen Jia-Chi, "Study of the disposable urea sensor and the pre-amplifier", June, 2002, Department of biomedical engineering, Chung Yuan Christian University, Master dissertation, pp.32-40; Liao Han-chou, "Novel calibration and compensation technique of circuit for biosensors", Master dissertation, Department of electrical engineering, Chung Yuan Christian University, pp. 11-27, June, 2004; Chen Jheng-cheng, "study of using tin dioxide film to fabricate array type pH sensing device", June, 2003, Department of electrical engineering, Chung Yuan Christian University, Master dissertation, pp.47-65; Liao Hung-Kwei, "Application of tin oxide sensing film on ion selective field effect transistors, June 1998, Department of electrical engineering, Yuan Christian University, Ph. D. dissertation, pp. 23-42].

At present, wireless transmission technique and application has not been used in the pH measurement. Therefore, the present invention provides a convenient wireless pH measurement system to achieve the measurement of physiologic parameters and the design of real time environmental monitoring system.

SUMMARY OF THE INVENTION

The present invention is about to solve the technical issue in order to provide a lower-cost and more convenient measurement equipment for a user to know his health status. When the measurement result is beyond a normal range, further diagnosis and treatment are then taken place in a hospital. Therefore, clinic measurement equipments and man power can be more effectively utilized. Furthermore, a patient can monitor the concentrations of the eight important parameters of his own body so as to provide these data for a doctor to diagnose.

In order to solve the above-mentioned issue, the present invention discloses a wireless pH measurement system by integrating wireless Bluetooth technology and voltage type biomedical sensors. Semiconductor processes are utilized to fabricate pH measurement device. The measurement device integrated with wireless transmission technique is convenient for users and pH values can be easily measured without any distance limitation. Wireless transmission is convenient for household pH value measurement.

Compared to the prior art, because the present invention integrates voltage type biomedical sensors and wireless Bluetooth technology, a wireless pH measurement system is fabricated. The system integrated with Blue-tooth technology cooperates with a front-end pH sensor to form a complete wireless biosensor system. Thus, the present invention can be applied in medical measurement industry and environmental protection monitoring. The method and apparatus provide stable and unaffected data for a voltage type biomedical sensor.

Table 1 shows comparison of wireless transmission techniques.

Table 2 shows the measurement results of sensors.

DESCRIPTION OF THE PREFERRED EMBODIMENTS

Only the technique and elements required in the present invention are described in the following. However, it should be recognized that the present invention can be practiced by various techniques. For clarity, some part of the figures is not drawn in proportion, in which the size of some part has been exaggerated.

Figure 1A:
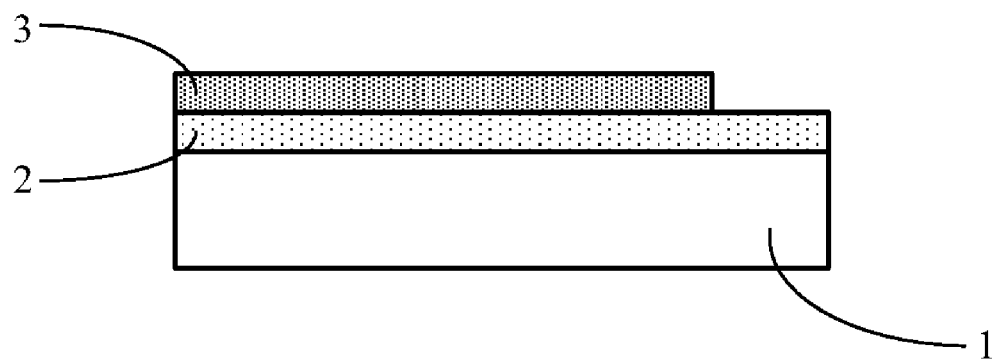
FIGS. 1A and 1B are schematic diagrams illustrating processes for fabricating a pH sensor by using acid-base ion selective electrode in a preferred example according to the present invention.
Figure 1B:
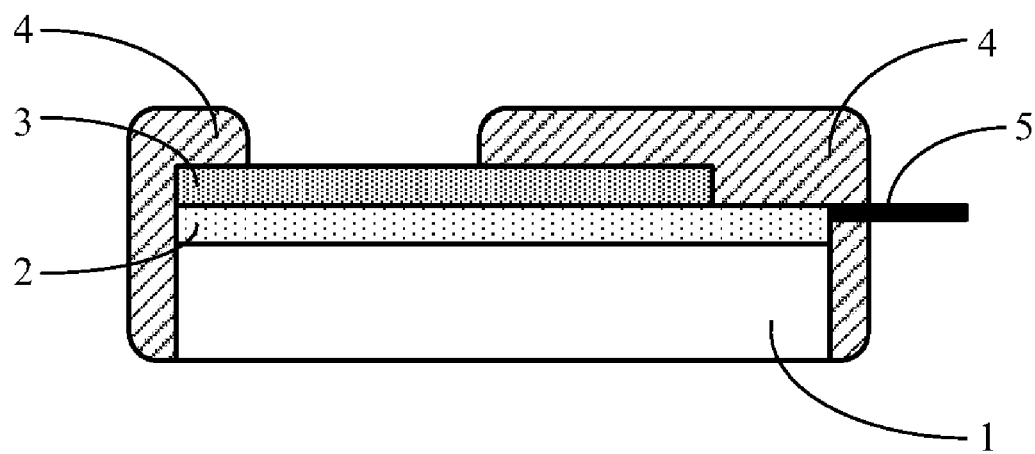

FIGS. 1A and 1B are schematic diagrams illustrating processes for fabricating a pH sensor by using acid-base ion selective electrode in a preferred example according to the present invention. As shown in FIG. 1A, an indium tin oxide film (ITO film) 2 is formed on a substrate 1. A sensing film 3 is formed on the indium tin oxide film 2. The preferred example shown in FIG. 1A comprises the following steps. At first, an indium tin oxide film is formed on a substrate. Preferably, the thickness of the indium tin oxide film is about 230 Å, but is not limited. The substrate is an insulation substrate, such as ceramic substrate, glass substrate. Glass substrate is preferred. The process for fabricating the sensing film 3 comprises depositing a tin dioxide ($SnO_2$) film by physical vapor deposition method. A RF (radio frequency) sputtering method is preferred and the sputtering target is tin dioxide. Preferred material for the sensing film is tin dioxide, but is not limited to tin dioxide. Mixture gas flows into the reaction chamber and the substrate is maintained at a temperature. Preferred mixture gas is mixture of argon and oxygen gas. The temperature of the substrate is preferably about 150° C. for depositing a tin dioxide ($SnO_2$) film, the deposition pressure is preferably about 20 mTorr, the RF power is preferably about 50 W, and the thickness of the film is preferably about 2000 Å.

As show in FIG. 1B, the sensing film 3 is connected to a conductive wire 5. A package material 4 covers the sensing film 3, the indium tin oxide film 2, and a portion of the substrate 1. The package material 4 comprises a sensing window to expose the sensing film 3. Next, a conductive wire is formed and packaging a sensing electrode is carried out. The conductive wire is preferably a silver wire. The conductive wire is adhered to the tin dioxide film via silver paste. The packaging material is preferably epoxy resin but can be other suitable material. Preferably, the epoxy resin sensing widow has an area of 2×2 mm².

Figure 2:
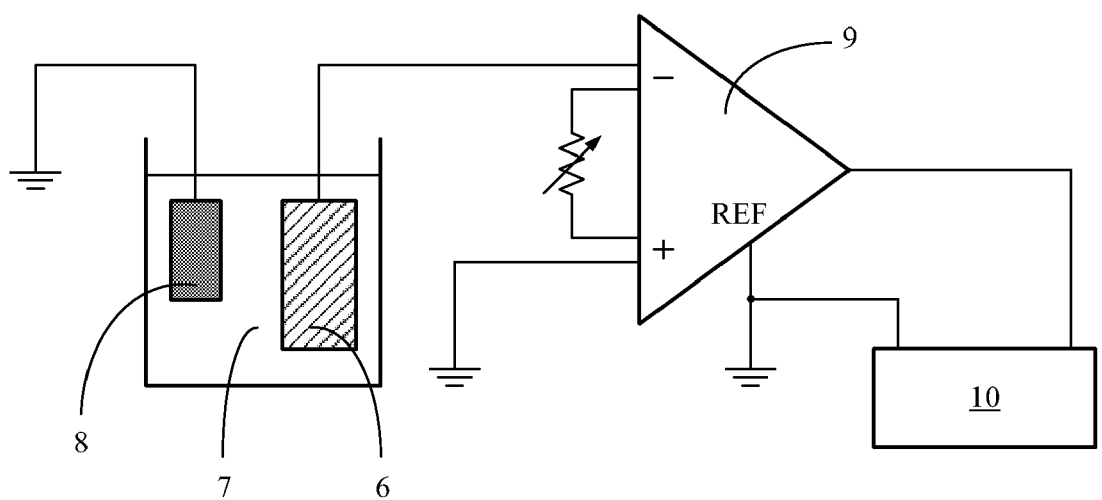
FIG. 2 is a measurement construction diagram for the potentiometric pH measurement system in a preferred example according to the present invention.

FIG. 2 is a measurement construction diagram for the potentiometric pH measurement system in a preferred example according to the present invention. The signal detecting and processing circuit for a sensor 6 shown in FIG. 2 comprises an amplifier 9. The amplifier 9 is connected to the sensor 6 with its negative input terminal and is used to measured the reaction potential of the sensor, together with an electrode 8 providing stable reference potential. The sensor 6 combined with the electrode 8 is to measure the pH value of an unknown buffer solution 7 and the result is transmitted to a digital multimeter 10. The electrode 8 is preferably a silver/silver chloride glass electrode but can be other electrode material. This example uses tin dioxide/indium tin oxide/glass substrate as the basic structure and uses a silver/silver chloride electrode to provide stable reference potential so as to measure the reaction potential of the sensor placed in the unknown solution 7. The example shown in FIG. 2 is only one of the embodiments of the present invention and is not used to limit the scope of the invention. It is obvious to those skilled in the art that many modifications of the present invention may be made without departing from what is intended to be limited solely by the appended claims.

Figure 3:
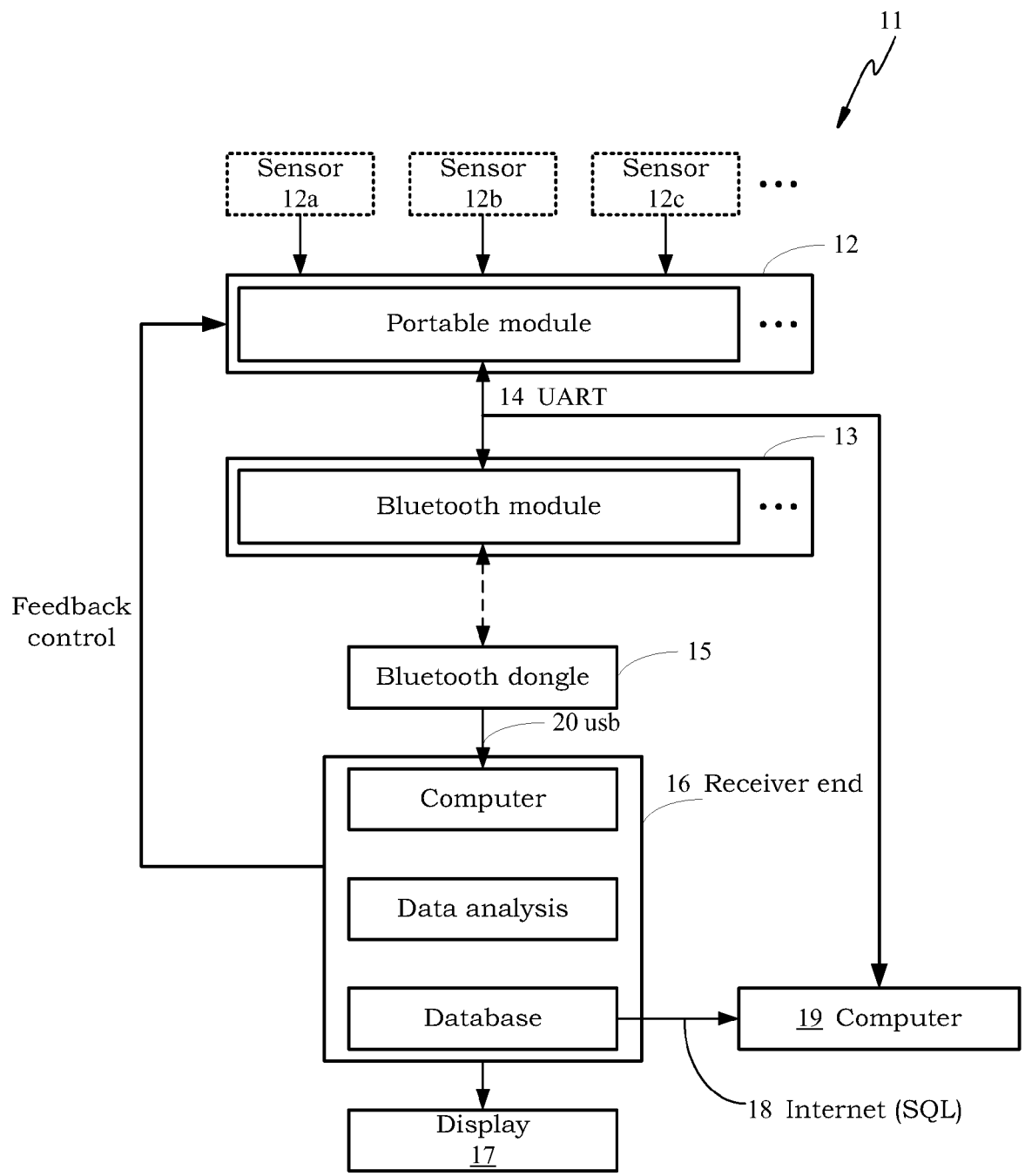
FIG. 3 is a system construction diagram of the intelligent Bluetooth wireless pH measurement system in a preferred example according to the present invention; and, FIG. 4 shows the accuracy of the measurement results from the pH sensor in a preferred example according to the present invention.

FIG. 3 is a system construction diagram of the intelligent Bluetooth wireless pH measurement system in a preferred example according to the present invention. As shown in FIG. 3, the wireless pH measurement system is based on a pH sensor, i.e. a portable module, and a Bluetooth module. The portable module comprises two portions, the first portion is a signal detecting and processing portion and the second portion is a wireless transmission portion. The first portion, i.e. the signal detecting and processing portion, detects a physiological signal by a pH sensor and amplifies the signal to the needed scale by the amplifier. A filter is used to process the signal for filtering out the noise and reducing the amplification. The signal is then transmitted to a microprocessor to carry out analog/digital conversion and numerical processes. Finally, it is wirelessly transmitted by the Bluetooth module of the second portion. The wireless pH measurement system further comprises a receiver end for receiving data by a commercial Bluetooth transmitter and processes the data by programs, displays, analyzes and stores the data. A warning signal is generated to notify a doctor about the status of the patient when an abnormal value is received. The amplifier, filter, and microprocessor are only examples for the elements in the portable module but these do not restrict the scope of the elements in the portable module. The elements with the functions equal to the amplifier, filter, and microprocessor are not excluded from the scope of the invention. A portable module 12 in a wireless pH measurement system 11, i.e. pH measurement system shown in FIG. 2, detects signals by sensors 12a, 12b, and 12c and transmits the signals to a Bluetooth module 13 via a transmission interface 14. The portable module 12 can also transmit the signals to a computer 19 via the transmission interface 14. The Bluetooth module 13 carries out wireless transmission and transmits the signals to a Bluetooth dongle 15 (or called Bluetooth receiver/transmitter) of a receiver end 16. The Bluetooth dongle 15 transmits the signals via a transmission interface 20 to a computer in the receiver end 16. The receiver end 16 uses a computer to analyze data and stores data in a data base. The Bluetooth dongle 15 can receives the data from the Bluetooth module 13 at the computer end and transmits command codes. The data can be transmitted to the computer 19 via internet 18 or displayed by a display 17. The transmission interfaces 14 and 20 comprise Universal Serial Bus (USB) and Universal Asynchronous Receiver/Transmitter (UART). The Bluetooth module 13 and the Bluetooth dongle 15 are not necessarily included in the portable module 12 and the receiver end 16. The Bluetooth module 13 and the Bluetooth dongle 15 can be treated as a wireless transmission module. The Bluetooth module 13 and the Bluetooth dongle 15 as well as the portable module 12 and the receiver end 16 are major components of the wireless pH measurement system according to the present invention. The Bluetooth module 13 and the Bluetooth dongle 15 are only examples for wireless transmission modules but these do not restrict the scope of the components in the wireless transmission module. The components with the functions equal to the Bluetooth module 13 and the Bluetooth dongle 15 are not excluded from the scope of the invention.

Figure 4:
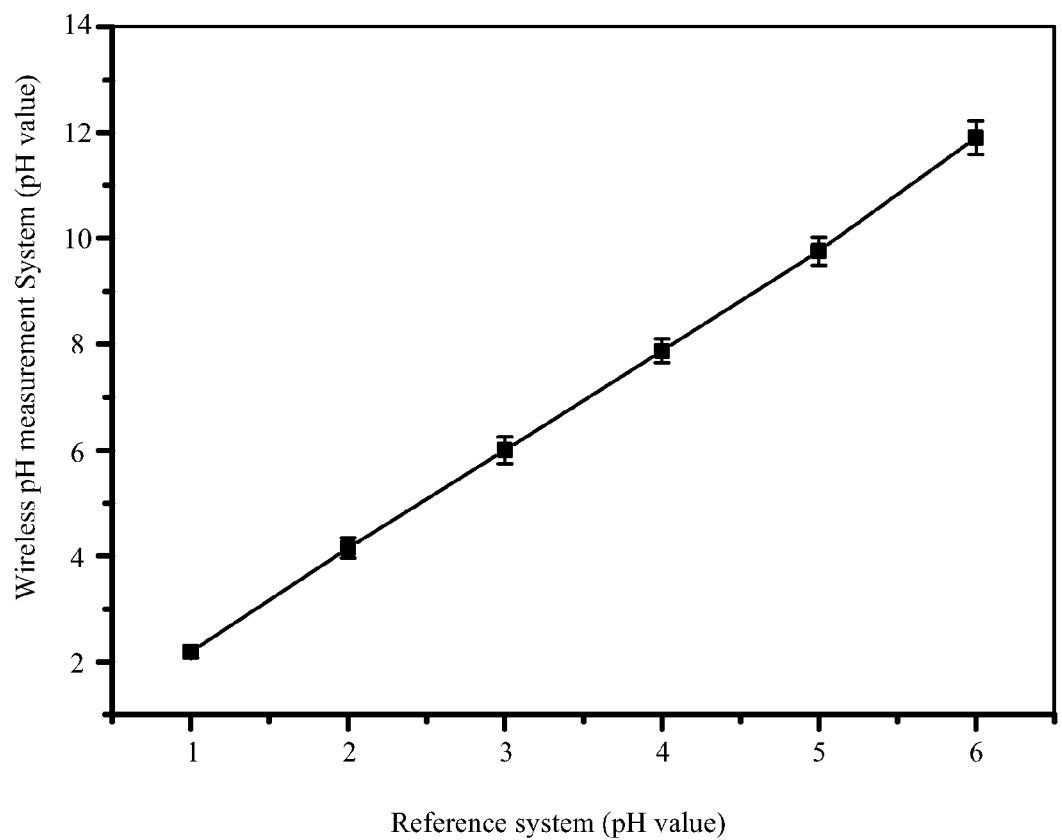

FIG. 4 shows the accuracy of the measurement results from the pH sensor in a preferred example according to the present invention. As shown in FIG. 4, the measurement construction shown in FIG. 3 is used to detect the pH sensor shown in FIG.

1. Ten pH sensors are sequentially placed in pH2~pH12 buffer solutions. After voltages are stabilized, the voltage values of the pH sensors are transmitted to a computer via a Bluetooth module. The computer receives data via a Bluetooth transmitter and performs displaying and recording operations. Finally, the results of the ten pH sensors are compared with that of a commercial wired pH sensor. A slanted line in FIG. 4 is the measurement result from the commercial wired pH sensor while the squares on the slanted line are the calculation results from the ten pH sensors. The calculation results shown in Table 2 are very close to the measurement result from the commercial wired pH sensor.

Table 1 shows comparison of wireless transmission techniques. As shown in Table 1, currently four types of wireless transmission techniques comprise Bluetooth, IrDA, home RF, and IEEE802.11 techniques. The IrDA technique has lower cost but its transmission distance is limited. Home RF and IEEE802.11 techniques have longer transmission distance but their costs are high. The Bluetooth technique can select the required transmission distance and has lower cost than home RF and IEEE802.11. The specification for each of these four wireless transmission types is for different market sector and the utilized technique is also different.

Table 2 shows the measurement results of sensors. As shown in Table 2, the measurement results of the ten pH sensors are obtained by sequentially placing the ten pH sensors in pH2~pH12 buffer solutions. After voltages are stabilized, the voltage values of the pH sensors are transmitted to a computer via a Bluetooth module. The computer receives the values via the Bluetooth transmitter and carries out numerical process.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A wireless pH measurement system, comprising:
a portable module and a receiver end;
wherein said portable module comprises:
  a signal detecting and processing portion comprising a sensor unit for detecting a pH signal, amplifying, filtering noise, analog/digital conversion and numerical processing to generate a pH measurement signal, and
  a wireless transmission portion receiving said pH measurement signal via a transmission interface and transmitting by a BLUETOOTH module; and said receiver end comprises a BLUETOOTH receiver for receiving said pH measurement signal and said receiver end processes said pH measurement signal by programs, displays, analyzes, and stores said pH measurement signal and transmits warning signal when an abnormal pH measurement signal is received.

2. The system according to claim 1, wherein said sensor unit comprises a substrate, an indium tin oxide film on said substrate, a sensing film on said indium tin oxide film and connected to a conductive wire, an electrode, and a package material covering said sensing film, said indium tin oxide film, and a portion of said substrate and exposing the sensing film via a sensing window.

3. The system according to claim 2, wherein said sensing film comprises a tin dioxide film and said tin dioxide film is deposited on said indium tin oxide film and said substrate by a RF (radio frequency) sputtering method.

4. The system according to claim 3, wherein the thickness of said tin dioxide film is about 2000 Å.

5. The system according to claim 2, wherein said substrate comprises a glass substrate.

6. The system according to claim 2, wherein said conductive wire comprises a silver wire.

7. The system according to claim 6, wherein said silver wire is adhered to said sensing film via silver paste.

8. The system according to claim 2, wherein said package material comprises epoxy resin.

9. The system according to claim 2, wherein said electrode comprises a silver/silver chloride glass electrode.

10. The system according to claim 2, wherein said sensing window has an area of $2 \times 2$ mm$^2$ on said package material.

11. The system according to claim 1, wherein said signal detecting and processing portion comprises:
an amplifier for analog processing and access to said pH measurement signal;
a microprocessor for receiving said pH measurement signal from said amplifier to carry out analog/digital conversion and performing numerical processing to generate said pH measurement signal.

12. The system according to claim 1, wherein said transmission interface comprises either Universal Serial Bus (USB) or Universal Asynchronous Receiver/Transmitter (UART).

13. The system according to claim 1, wherein said receiver end further comprises a transmission interface, a computer, a data base in which said measurement signal is transmitted to said computer via said transmission interface to carry out data analysis or to store in said data base.

14. The meter according to claim 13, wherein said transmission interface comprises either Universal Serial Bus (USB) or Universal Asynchronous Receiver/Transmitter (UART).

15. A wireless pH measurement system, comprising:
a portable module and a receiver end;
wherein said portable module comprises:
  a signal detecting and processing portion comprising a sensor unit for detecting a pH signal, amplifying, filtering noise, analog/digital conversion and numerical processing to generate a pH measurement signal, and
  a wireless transmission portion comprising a BLUETOOTH module for receiving said pH measurement signal via a transmission interface and transmitting said pH measurement signal and a BLUETOOTH receiver module for receiving said pH measurement signal; and
said receiver end receives said pH measurement signal from said BLUETOOTH receiver module via another transmission interface and processes said pH measurement signal by programs, displays, analyzes and stores said pH measurement signal and transmits warning signal when an abnormal pH measurement signal is received.

16. The system according to claim 15, wherein said sensor unit comprises a substrate, an indium tin oxide film on said substrate, a sensing film on said indium tin oxide film and connected to a conductive wire, an electrode, and a package material covering said sensing film, said indium tin oxide film, and a portion of said substrate and exposing the sensing film via a sensing window.

17. The system according to claim 16, wherein said sensing film comprises a tin dioxide film and said tin dioxide film is deposited on said indium tin oxide film and said substrate by a RF (radio frequency) sputtering method.

18. The system according to claim 17, wherein the thickness of said tin dioxide film is about 2000 Å.

19. The system according to claim 16, wherein said substrate comprises a glass substrate.

20. The system according to claim 16, wherein said conductive wire comprises a silver wire.

21. The system according to claim 20, wherein said silver wire is adhered to said sensing film via silver paste.

22. The system according to claim 16, wherein said package material comprises epoxy resin.

23. The system according to claim 16, wherein said electrode comprises a silver/silver chloride glass electrode.

24. The system according to claim 16, wherein said sensing window has an area of 2×2 mm$^2$ on said package material.

25. The system according to claim 15, wherein said signal detecting and processing portion comprises:
   an amplifier for analog processing and access to said pH measurement signal;
   a microprocessor for receiving said pH measurement signal from said amplifier to carry out analog/digital conversion and performing numerical processing to generate said pH measurement signal.

26. The system according to claim 15, wherein said transmission interface comprises either Universal Serial Bus (USB) or Universal Asynchronous Receiver/Transmitter (UART).

27. The system according to claim 15, wherein said receiver end further comprises a transmission interface, a computer, a data base in which said measurement signal is transmitted to said computer via said transmission interface to carry out data analysis or to store in said data base.

* * * * *